(12) United States Patent
Wu et al.

(10) Patent No.: US 10,854,317 B2
(45) Date of Patent: Dec. 1, 2020

(54) METHOD AND SYSTEM FOR SEQUENCE ALIGNMENT AND VARIANT CALLING

(71) Applicant: ACT Genomics Co., Ltd., Taipei (TW)

(72) Inventors: Ko-Wen Wu, Taipei (TW); Kun-Lin Li, Taipei (TW)

(*) Notice: Subject to any disclaimer, the term of this patent is extended or adjusted under 35 U.S.C. 154(b) by 0 days.

(21) Appl. No.: 16/479,928

(22) PCT Filed: Dec. 28, 2018

(86) PCT No.: PCT/CN2018/125053
§ 371 (c)(1),
(2) Date: Jul. 23, 2019

(87) PCT Pub. No.: WO2019/129239
PCT Pub. Date: Jul. 4, 2019

(65) Prior Publication Data
US 2019/0385701 A1  Dec. 19, 2019

Related U.S. Application Data

(60) Provisional application No. 62/611,698, filed on Dec. 29, 2017.

(51) Int. Cl.
*G16B 30/10* (2019.01)
*G16B 20/20* (2019.01)
*C12Q 1/6869* (2018.01)

(52) U.S. Cl.
CPC ........... *G16B 30/10* (2019.02); *C12Q 1/6869* (2013.01); *G16B 20/20* (2019.02)

(58) Field of Classification Search
None
See application file for complete search history.

(56) References Cited

U.S. PATENT DOCUMENTS

2011/0270533 A1* 11/2011 Zhang ................ G16B 30/00
702/20
2012/0252682 A1  10/2012 Zhou et al.

FOREIGN PATENT DOCUMENTS

| CN | 104357563 A | 2/2015 | |
|---|---|---|---|
| CN | 105714383 A | 6/2016 | |
| CN | 107385042 A | 11/2017 | |
| CN | 107480472 A | 12/2017 | |
| WO | WO-2016038220 A1 * | 3/2016 | ........... C12Q 1/6883 |
| WO | WO2016038220 A1 | 3/2016 | |

OTHER PUBLICATIONS

Li et a. in Bioinformatics (2009) vol. 25:1754-1760.*
Schroder et al. in Bioinformatics (2014) vol. 30:1064-1072.*
Tang et al. (2017) Ti: AASRA: An Anchor Alignment-Based Small RNA Annotation Pipeline in bioRxiv doi: https://doi.org/10.1101/132928.*
Markoulatos et al. (Journal of Clinical Laboratory Analysis (2002) vol. 16:47-51).*
Zheng et al. (Nature Medicine (2013) vol. 20, No. 12:1479-1485).*

* cited by examiner

*Primary Examiner* — Lori A. Clow
(74) *Attorney, Agent, or Firm* — Opes IP Consulting Co. Ltd.

(57) ABSTRACT

A method to align a next generation sequencing read to a reference sequence includes: (a) receiving a sequencing read; (b) performing a first alignment of the sequencing read to a reference sequence so as to identify a target sequence within the reference sequence whereto the sequencing read maps; (c) selecting a first and a second anchor sequence; (d) attaching the first anchor sequence to the upstream region of the sequencing read and the second anchor sequence to the downstream region of the sequencing read so as to generate an extended sequencing read; (e) attaching the first anchor sequence to the upstream region of the target sequence and the second anchor sequence to the downstream region of the target sequence, so as to generate an extended target sequence; (f) performing a second alignment of the extended sequencing read to the extended target sequence, so that the second alignment is more correctly mapped to the target sequence than the first alignment; (g) identifying a position where one or more bases between the extended sequencing read and the extended target sequence are different based on the second alignment result; and (h) calling a variant based on the identification in step (g).

17 Claims, 1 Drawing Sheet
Specification includes a Sequence Listing.

(a)
Misalignment:                    1         11        21        31
Reference Sequence:   AACAAGCTCTTTCTTTCTCTGTTTTAAGATCT
                                          |    |  |||||||||
Sequencing Read:      ------------------AACAAGCTCTTAAGATCT
(b)
Misalignment with soft-clipping:
Reference Sequence:   AACAAGCTCTTTCTTTCTCTGTTTTAAGATCT
                                                |||||||||
Sequencing Read:                        AACAAGCTCTTAAGATCT
(c)                                     Soft-clipped region
Correct alignment:
Reference Sequence:   AACAAGCTCTTTCTTTCTCTGTTTTAAGATCT
                      |||||||||                |||||||||
Sequencing Read:      AACAAGCTC---------------TTAAGATCT

Figure 1

SEQUENCE LISTING

<160> NUMBER OF SEQ ID NOS: 11

<210> SEQ ID NO 1
<211> LENGTH: 130
<212> TYPE: DNA
<213> ORGANISM: Homo sapiens

<400> SEQUENCE: 1

```
cctttctctc ctcatacctc ccctcacctg cctggcatcc gaggcccttc cccgtccect      60 gttggctctc ccgccagtgt tgctcagtct cgctcaggac cactctcgcc tgctgcagtg     120
ccaggtaccc                                                            130
```

<210> SEQ ID NO 2
<211> LENGTH: 132
<212> TYPE: DNA
<213> ORGANISM: Homo sapiens

<400> SEQUENCE: 2

```
cacctggagt gagccctgct ccccctggc tccttcccag cctgggcatc cttgagttcc       60
aaggcctcat tcagctctcg gaacatctcg aagcgctcac gcccatctcg aagcgctcac     120
gcccacggat ct                                                         132
```

<210> SEQ ID NO 3
<211> LENGTH: 20
<212> TYPE: DNA
<213> ORGANISM: Homo sapiens

<400> SEQUENCE: 3

```
catctcgaag cgctcacgcc                                                  20
```

<210> SEQ ID NO 4
<211> LENGTH: 118
<212> TYPE: DNA
<213> ORGANISM: Homo sapiens

<400> SEQUENCE: 4

```
gtggtgggga agcaggtgag tcctcaggtg gtggggatgt gggggagtcc tcaggtggtg      60
gggagaggcg tgaagcctca ggtggagggg acgtgggaga ctcctcaggc ggtgggga      118
```

<210> SEQ ID NO 5
<211> LENGTH: 93
<212> TYPE: DNA
<213> ORGANISM: Homo sapiens

<400> SEQUENCE: 5

```
tagggactct ggatcccaga aggtgagaaa gttaaaattc ccgtcgctat caaggaatta      60
agagaagcaa catctccgaa agccaacaag gaa                                   93
```

<210> SEQ ID NO 6
<211> LENGTH: 93
<212> TYPE: DNA
<213> ORGANISM: Homo sapiens

<400> SEQUENCE: 6

```
tagggactct ggatcccaga aggtgagaaa gttaaaattc ccgtcgctat caaggaatta      60
agagaagcaa catctccgaa agccaacaag gaa                                   93
```

<210> SEQ ID NO 7
<211> LENGTH: 123

```
<212> TYPE: DNA
<213> ORGANISM: Homo sapiens

<400> SEQUENCE: 7
caagctcttt ctttctctct gttttaagat ctgggcagtg aattagttcg ctacgatgca      60
agagtacaca ctcctcattt ggataggctt gtaagtgccc gaagtgtaag cccaactaca     120
gaa                                                                   123

<210> SEQ ID NO 8
<211> LENGTH: 89
<212> TYPE: DNA
<213> ORGANISM: Homo sapiens

<400> SEQUENCE: 8
ggcactgggt caaagtctcc tggggcccat gatagccgtc tttaacaagc tctttctttc      60
tctctgtttt aagatctggg cagtgaatt                                        89

<210> SEQ ID NO 9
<211> LENGTH: 198
<212> TYPE: DNA
<213> ORGANISM: Escherichia coli

<400> SEQUENCE: 9
agcttttcat tctgactgca acgggcaata tgtctctgtg tggattaaaa aaagagtctc      60
tgacagcagc ttctgaactg gttacctgcc gtgagtaaat taaaatttta ttgacttagg     120
tcactaaata ctttaaccaa tataggcata gcgcacagac agataaaaat tacagagtac     180
acaacatcca tgaaacgc                                                   198

<210> SEQ ID NO 10
<211> LENGTH: 34
<212> TYPE: DNA
<213> ORGANISM: Artificial Sequence
<220> FEATURE:
<223> OTHER INFORMATION: example sequence

<400> SEQUENCE: 10
aacaagctct ttctttctct ctgttttaag atct                                  34

<210> SEQ ID NO 11
<211> LENGTH: 18
<212> TYPE: DNA
<213> ORGANISM: Artificial Sequence
<220> FEATURE:
<223> OTHER INFORMATION: Example sequence

<400> SEQUENCE: 11
aacaagctct taagatct                                                    18
```

METHOD AND SYSTEM FOR SEQUENCE ALIGNMENT AND VARIANT CALLING

CROSS REFERENCE TO THE RELATED APPLICATION

The present application claims priority to U.S. Provisional Application Ser. No. 62/611,698 filed on Dec. 29, 2017, which is incorporated by reference in their entirety.

FIELD OF THE INVENTION

This disclosure is related to the fields of bioinformatics, next-generation sequencing, and disease detection.

BACKGROUND THE INVENTION

Next-generation DNA sequencing (NGS) has become a powerful tool for reading sequences from clinical samples. Ultra-deep sequencing is the method of using NGS to sequence a sample to a high depth of coverage in order to determine rare sequence variants. Sequence variants can be the key to determine the status of a personal trait or disease, for instance, cancer, rare genetic diseases, or complex diseases. Therefore, it is important to call sequence variants accurately.

To determine sequence variants, NGS analysis methods align NGS sequencing reads from a given sample to a reference genome to identify positions where the sequence in the sample differs from the reference. In some NGS methods, adaptor sequences are added to the ends of each sequencing template for sequencing purposes. These adaptor sequences are not part of the sample for interrogation. During analysis, the adaptor sequences are removed from the ends of the sequencing reads through a step called adaptor trimming. Adaptor trimming is not perfect and may retain part of the adaptor sequence on the sequencing read without trimming. Therefore, conventional alignment methods perform soft-clipping when it detects a sudden poor alignment to the reference sequence towards the end of a read. After soft-clipping, the sequence starting from the sudden poorly aligned position is hidden from alignment and not considered for further analysis.

In some circumstances, the poor alignment is not due to sequencing of adaptor sequences, but because there are insertions or deletions occurring at the point of detection. This occurs more often when there is a variant near the end of a read, and may be especially problematic when the variant is several nucleotides long. In those cases, soft-clipping causes the sequence following that point to be hidden from analysis and the variants in those regions cannot be called. However, true variants that cause diseases or traits may lie within the region that are soft-clipped and will be missed by the variant caller. In order to detect the variants in these regions, there is a need for new alignment and variant calling methods.

SUMMARY OF THE INVENTION

In this disclosure, an alignment method is introduced to solve misalignments and soft-clipping problems in NGS sequence alignment. Briefly, a first alignment is performed to map the NGS sequencing reads to a reference genome and identify a target sequence region for each sequencing read. However, this first alignment may be imperfect due to underlying variants within the sequencing sample, which causes the sequencing reads to map to neighboring positions and/or open wrong gaps, resulting in misalignment or soft-clipping. This situation occurs particularly often when the variant is close to the end of the sequencing read. To solve the above issue, anchor sequences are added to each side of the sequencing reads and the target region on the reference sequences that they map to for a second alignment step. By adding the same sequence to the sequencing reads and the target sequences ensures that when a second alignment is performed, the sequencing reads map perfectly to the correct region onto the reference sequence. The correct second alignment is obtained by creating a high score in the alignment of the anchor sequences in the extended sequencing reads to the identical anchor sequences in the extended target sequence, so that the sequencing reads are forced to align to the correct region of the reference sequence without creating mismatches or opening unnecessary gaps. In this corrected second alignment, there are more nucleotides at the end of the sequencing read that are mapped to the target sequence than in the first alignment. FIG. 1 shows an example of a sequencing read mapped onto its target sequence. In a first alignment, there may be a misalignment as shown in FIG. 1(a). In this alignment, the poorly aligned region may be soft-clipped as shown in FIG. 1(b). The correct alignment obtained after a second alignment is shown in FIG. 1(c). In the correct second alignment, the gaps are in the middle of the read showing a deletion variant. In the correct second alignment, there are more matching nucleotides than in the first alignment. In the correct second alignment, there are more total nucleotides that are aligned to the reference target sequence than in the first alignment. In the first alignment, there are many consecutive mismatches in FIG. 1(a), and are soft-clipped in FIG. 1(b). In the first alignment, a stretch of consecutive nucleotides at the end of the sequencing read is poorly aligned to the target sequence and resulted in mismatches. In the correct second alignment, those nucleotides are mapped to another region in the target sequence which results in matches. Because the adjacent regions are mapped perfectly to the target sequence, the variant positions within the sequencing reads are forced to map to the corresponding position in the target sequence with a gap or mismatch instead of mapping incorrectly to a neighboring base with a match or opening unnecessary gaps. Through the corrected second alignment, variant positions are mapped to the correct position on the target sequence, and the difference between the two can be correctly called as a variant, whether it is an insertion, deletion, or substitution. Therefore, the second alignment using anchor sequences allows the detection of variants that were not detected using conventional alignment methods. The present disclosure provides a method and system for aligning NGS sequencing reads to a reference sequence including the following steps: (a) receiving a sequencing read; (b) performing a first alignment of the sequencing read to a reference sequence so as to identify a target sequence within the reference sequence whereto the sequencing read map; (c) selecting a first and a second anchor sequence; (d) attaching the first anchor sequence to the upstream region of the sequencing read and the second anchor sequence to the downstream region of the sequencing read so as to generate an extended sequencing read; (e) attaching the first anchor sequence to the upstream region of the target sequence and the second anchor sequence to the downstream region of the target sequence, so as to generate an extended target sequence; and (f) performing a second alignment of the extended sequencing read to the extended target sequence, so that the second alignment is more correctly mapped to the target sequence than the first alignment.

The present disclosure also provides a system to call one or more variants from a sequencing read. The method that the system used to call the variants includes the following steps: (a) receiving a sequencing read; (b) performing a first alignment of the sequencing read to a reference sequence so as to identify a target sequence within the reference sequence whereto the sequencing read map; (c) selecting a first and a second anchor sequence; (d) attaching the first anchor sequence to the upstream region of the sequencing read and the second anchor sequence to the downstream region of the sequencing read so as to generate an extended sequencing read; (e) attaching the first anchor sequence to the upstream region of the target sequence and the second anchor sequence to the downstream region of the target sequence, so as to generate an extended target sequence; (f) performing a second alignment of the extended sequencing read to the extended target sequence, (g) identifying a position where one or more bases between the extended sequencing read and the extended target sequence is different based on the second alignment result; and (h) calling a variant based on the identification in step (g).

In some embodiments, the sample originates from cell line, biopsy, primary tissue, frozen tissue, formalin-fixed paraffin-embedded (FFPE), liquid biopsy, blood, serum, plasma, buffy coat, body fluid, visceral fluid, ascites, paracentesis, cerebrospinal fluid, saliva, urine, tears, seminal fluid, vaginal fluid, aspirate, lavage, buccal swab, circulating tumor cell (CTC), cell-free DNA (cfDNA), circulating tumor DNA (ctDNA), DNA, RNA, nucleic acid, purified nucleic acid, purified DNA, or purified RNA.

In some embodiments, the sample is a clinical sample. In some embodiments, the sample originates from a diseased patient. In some embodiments, the sample originates from a patient having cancer, solid tumor, hematologic malignancy, rare genetic disease, complex disease, diabetes, cardiovascular disease, liver disease, or neurological disease. In some embodiments, the sample originates from a pregnant woman, a child, an adolescent, an elder, or an adult. In some embodiments, the sample is a research sample. In some embodiments, the sample originates from a mammal, reptile, amphibian, fish, insect, worm, a single cellular organism, yeast, bacteria, archaea, or an environmental sample. In some embodiments, the sample originates from a group of samples. In some embodiments, the group of samples is from related species. In some embodiments, the group of samples is from different species.

In some embodiments, the sequencing reads are generated by genome resequencing, targeted sequencing, epigenetic sequencing, transcriptome sequencing, chromatin immunoprecipitation followed by sequencing (ChIP-seq), or chromosome conformation capture followed by sequencing (Hi-C).

In some embodiments, the sequencing reads are generated from nucleic acids that are captured by a bait from the original sample. The bait can be a nucleic acid that hybridizes to the sequence of interest to capture and enrich in the sequence of interest. In some embodiments, the sequencing reads are generated from nucleic acids that are amplified from the original sample or the nucleic acids captured by the bait. In some embodiments, the sequencing reads are generated from a sequencing run that used an adapter sequence.

In some embodiments, the sequence of the sample is compared to a reference genome or a reference sequence. In some embodiments, the reference genome or reference sequence is a normal tissue sample. In some embodiments, the reference genome or reference sequence is the genome sequence of an individual. In some embodiments, the reference genome is the consensus sequence of a species. In some embodiments, the reference genome is the human genome. In some embodiments, the reference genome is from the same individual as the sample. In some embodiments, the reference genome is from a different individual from the sample. In some embodiments, the reference genome is from a related individual to the sample. In some embodiments, the reference genome is from the same cell type or tissue as the sample. In some embodiments, the reference genome is from a different cell type or tissue as the sample.

In some embodiments, a portion of the sequencing reads is soft-clipped in the first alignment. In some embodiments, at least one variant is present in the region of the sequencing read that was soft-clipped. In the second alignment, by using anchor sequences, the variant is not soft-clipped.

In some embodiments, the sequenced sample comprises a variant. In some embodiments, the sequenced sample is a complex sequence region. In some embodiments, the sequenced region comprises repetitive sequences. In some embodiments, the variant is a germline variant. In other embodiments, the variant is a somatic variant. In some embodiments, the variant originates from a fetal cell or fetal nucleic acids within a mother's sample. In some embodiments, the variant causes, correlates with, or is related to a disease. In some embodiment, the variant is related to cancer, cardiovascular disease, metabolic syndrome, neurological disease, or immune status. In some embodiments, the variant indicates a personal trait, intellectual propensity or potential, or an ancestral lineage. In some embodiments, the variant is an insertion, a deletion, or a combination thereof. In some embodiments, the variant is located within 1, 2, 3, 4, 5, 6, 7, 8, 9, 10, 11, 12, 13, 14, 15, 16, 17, 18, 19, 20, 25, 30, 35, 40, 45, or 50 nucleotides from the end of the sequencing read. In some embodiments, the variant is an insertion, a deletion, or a combination thereof having a variant length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 30, 45, 50, 55, 60, 65, 70, 75, 80, 85, 90, 95, 100, 120, 125, 130, 140, 150, 160, 170, 180, 190, 200, or 250 nucleotides. In some embodiments, the variant is at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% the length of the sequencing read. This method is particularly useful for detecting long insertion or deletion variants of 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 nucleotides or above. In some embodiments, the variant is a minor allele. In some embodiments, the variant is a major allele. In some embodiments, the variant has an allele frequency of at least 1, 5, 10, 15, 20, 25, 30, 50, or 60%. The sequencing instrument used to generate the sequencing reads may affect results for variant calling. In general, the allele frequency is greater than the error rate of the sequencing instrument. For example, if the sequencing instrument has a raw error rate of 5%, this method can be used to accurately call a variant with at least 5% allele frequency.

In some embodiments, the first anchor sequence, the second anchor sequence, or both are artificial sequences. In some embodiments, the first anchor sequence, the second anchor sequence, or both are sequences that do not align to the target sequence. In some embodiments, the first anchor sequence or the second anchor sequence has less than 90, 80, 70, 60, 50, 40, 30, 20, 15, 10, 5% identity to any part of the target sequence. In some embodiments, the first anchor sequence or the second anchor sequence comprises the adapter sequence for NGS sequencing. In some embodiments, the first anchor sequence maps to the target sequence immediately upstream of a sequencing read. In some embodiments, the second anchor sequence maps to the target sequence immediately downstream of a sequencing read. In some embodiments, a segment of nucleotides with IUPAC code N is inserted between the first or the second anchor sequence and the attached sequencing read, or between the first or the second anchor sequence and the attached target sequence. In some embodiments, the first or the second anchor sequence comprises of a IUPAC code N nucleotide. In some embodiments, the last nucleotide in the first anchor sequence or the first nucleotide in the second anchor sequence is IUPAC code N. In some embodiments, the anchor sequence maps to the primer sequence, wherein the primer is used for amplifying the targeted sequencing read. In some embodiments, the anchor sequences map to sequences that do not exist in the target sequence. In some embodiments, the anchor sequences are bacterial sequences. In some embodiments, the anchor sequences are E. coli genomic sequences. In some embodiments, the length of the first anchor sequence equals the length of the second anchor sequence. In some embodiments, the first anchor sequence is the reverse complement of the second anchor sequence. In some embodiments, the first anchor sequence or the second anchor sequence has a length that is at least 0.1, 0.25, 0.5, 0.75 or 1 time the length of the sequencing read. In some embodiments, the first anchor sequence or the second anchor sequence is at least 1, 2, 3, 4, 5, 6, 7, 8, 9, 10, 11, 12, 13, 14, 15, 16, 17, 18, 19, 20, 25, 30, 35, 40, 45, 50, 60, 70, 75, 80, 90, 100, 120, 125, 150, 175, or 200 nucleotides in length. In some embodiments, the first anchor sequence or the second anchor sequence is at least 1, 1.5, 2 or 3 times the length of the variant length. In some embodiments, the length of the first or the second anchor sequence is greater than $$\frac{-GO - GE \cdot v}{m - mm} - d,$$

where v is the length of the variant, d is the distance between the variant and the end of the sequencing read, GO, GE, m, and mm are gap opening, gap extension, match, and mismatch scoring parameters for sequence alignment.

In some embodiments, the sequencing reads are short reads having sequencing lengths no more than 500, 450, 400, 300, 250, 200, 175, 150, 125, 100, 80, 75, 650, 60, 50, 45, 40, 35, 30, or 25 nucleotides.

The first or the second alignment can be performed using one of several alignment algorithms or software, for example, Burrows-Wheeler Aligner (BWA), BWA-MEM, BWA-SW, Bowtie, Stampy, Torrent Mapping Alignment Program (TMAP), or TopHat.

BRIEF DESCRIPTION OF THE DRAWINGS

FIG. 1 shows an example of a sequencing read (AACAAGCTCTTAAGATCT; SEQ ID NO:11) mapped onto its target sequence (AACAAGCTCTTTCTTTCTCT CTGTTTTAAGATCT; SEQ ID NO:10). FIG. 1(a) shows the case of a misalignment. FIG. 1(b) shows the case when there is soft clipping. FIG. 1(c) shows the correct alignment with a deletion variant.

DETAILED DESCRIPTION

Definitions

As used herein, the terms "sample", "specimen," or "biological sample" are used interchangeably, and refer to any composition that contains nucleic acids for sequencing. It can be from any organism or any part of a body or tissue.

As used herein, the term "variant" refers to a part of a nucleic acid sequence wherein the sequence in the sample of interest is different from a reference sequence.

As used herein, "aligning" and "mapping" a sequencing read to a reference sequence refers to the action of positioning the sequencing read so that the same nucleotides in the sequencing read and the reference sequence are aligned at the same position. This alignment may result in a "match" when the sequencing read and the reference sequence have the same nucleotide at the aligned position, a "mismatch" when the sequencing read and the reference sequence have different nucleotides at the aligned position, or a "gap" when a nucleotide in the sequencing read is mapped in between two nucleotides in the reference sequence or when a nucleotide in the reference sequence is mapped between two nucleotides in the sequencing read.

As used herein, "reference genome" or "reference sequence" refers to a genome that is used as a reference for sequence alignment. It may be obtained from various sources, for example, a consensus genome sequence in the public database, a sample from an individual, or a cell line, to name a few but not to limit its scope.

As used herein, "target sequence" refers to part of a reference sequence where the sequencing read aligns.

As used herein, the distance of a variant to an end of a sequencing read is calculated from the closest point of the variant to the end of a sequencing read. If the variant is closer to the 5'-end of a sequencing read, the distance is calculated from the starting position of the variant, whether it is an insertion or deletion. If the variant is closer to the 3'-end of a sequencing read, the distance is calculated from the ending position of the variant, which equals to the starting position plus the length of the variant. The distance of the variant to an end of the sequencing read is the shorter length of the two calculations above.

EXAMPLES

Example 1. Detection of Missing Variants Using Anchor Alignment

Two formalin-fixed paraffin-embedded (FFPE) samples were obtained from a patient with cholangiocarcinoma and a patient with glioblastoma multiforme to identify the mutations in the samples which may have caused the disease. Genomic DNA was extracted using QIAamp® DNA FFPE Tissue Kit (QIAGEN®, Hilden, Germany). 80 ng of DNA was amplified using multiplexed PCR targeting 18,136 pairs of amplicons including one that covers the 7,876 bp region around the ARIDIA gene on chromosome 1. The samples were sequenced using Ion Proton™ (Thermo Fisher Scientific, Waltham, Mass.) system with the Ion PI Chip (Thermo Fisher Scientific, Waltham, Mass.) following manufacturer recommended protocol. Raw sequence reads were processed by the manufacturer provided software Torrent Variant Caller (TVC) v5.2 and .bam and .vcf files were generated. Table 1 lists two variants that were missed in the first alignment in the two samples, respectively.

In the first sample, around the ARIDIA gene, a 2-bp deletion occurred at chromosome 1 position 27087467 and was masked in some of the sequencing reads due to soft-clipping in this region when using the default settings of the TVC for sequence alignment.

In the first alignment, the total coverage of this position was 1405x, and the variant count was 90x, 88x from forward reads and 2× from reverse reads. The estimated variant frequency was 6.4% and strand bias was 0.96. Many reads in the reverse direction are soft-clipped starting from the variant position and were not included in the variant count in the reverse reads. Because this variant was not supported by at least three reads from each strand, it did not meet the criteria for calling it a variant.

The first 198 bp of *Escherichia coli* O157:H7 followed by a stretch of "NNNNN" (IUPAC code) was added to every read along this amplicon to the 5'-end as anchor sequence. Its reverse complement sequence was added to the 3'-end as anchor sequence. The resulting reference sequence is the 528-bp long extended reference sequence. Each read in this region is also extended by 198-bp on each end with the first 198 bp being exact matches to the reference sequence and the last 198 bp being exact matches to the reference sequence.

Local multiple sequence alignment was run using the BWA aligner v0.7.10 using the following parameters: bwa mem -k17 -W40 -r10 -A2 -B5 -O2 -E1 -L0. Alignment was performed for this region using the extended sequencing reads and extended reference sequence. In the resulting alignment, no variants were masked by soft-clipping. The variant counts at ARID1A chr1_27087467_TTC>T became 134×, 72× from forward reads and 62× from reverse reads. The total depth is 1523×. The variant frequency detected after anchor alignment is 8.8% and strand bias is 0.5. Using this method, this 2-bp deletion is detected with confidence. To confirm this variant, the same sample was sequenced using MiSeq sequencer (Illumina, San Diego, Calif.). Raw sequence reads were processed by MiSeq Reporter (Illumina, San Diego, Calif.) according to manufacturer's recommendation. The ARID1A chr1_27087467_TTC>T variant was detected and confirmed.

TABLE 1

Missing variant in sequencing reads

| Gene | Mutation Type | Allele Frequency | Amplicon Sequence (variant is underlined) |
|------|---------------|------------------|-------------------------------------------|
| ARID1A | Deletion | 8.80% | CCTT<u>TC</u>TCTCCTCATACCTCCCC TCACCTGCCTGGCATCCGAGGCC CTTCCCCGTCCCCTGTTGGCTCT CCCGCCAGTGTTGCTCAGTCTCG CTCAGGACCACTCTCGCCTGCTG CAGTGCCAGGTACCC (SEQ ID NO: 1) |
| TP53 | Insertion | 34.6% | CACCTGGAGTGAGCCCTGCTCCC CCCTGGCTCCTTCCCAGCCTGGG CATCCTTGAGTTCCAAGGCCTCA TTCAGCTCTCGGAA<u>CATCTCGAA GCGCTCACGCCC</u>ATCTCGAAGCG CTCACGCCCACGGATCT (SEQ ID NO: 2) |

In the second sample, around the TP53 gene, a 20-bp insertion (CATCTCGAAG CGCTCACGCC; SEQ ID NO:3) occurred at chromosome 17 position 7574006. In the first alignment following default parameters of TVC as described above, the total read count was 17839, of which 2430 reads supported the variant resulting in a variant allele frequency of 13.6%. All of the reads supporting the variant were in the reverse strand arriving at a strand bias of 1. A stretch of " " and the same anchors as described above were attached to the sequencing reads and the target sequence to generate the extended sequencing reads and extended target sequence. After a second alignment using the BWA aligner with the same parameters described above, these sequencing reads in the forward strand were correctly aligned to the target sequence. The total reads become 19287 with 6675 reads supporting the insertion, of which 4290 were in the forward strand and 2385 in the reverse strand resulting in a strand bias of 0.53. From this corrected second alignment, the insertion was detected with a variant allele frequency of 34.6%.

Example 2. Design of a First and Second Anchor Sequence for Aligning and Calling Various Sequence Variants In this example, we aim to find the parameters that determine how to design a good anchor sequence for this alignment and variant calling method. We demonstrate how the length of the anchor sequence must be longer than a threshold in order to force a correct alignment over the misalignment scenario. In the correct alignment, shown in FIG. 1c, there is a gap in the middle of the sequence. In the misalignment, shown in FIG. 1a, there is no gap. However, the region between the variant and the end of the sequencing read is misaligned to the reference sequence resulting in several mismatches. When an anchor is added to the end of the sequencing read and the target sequence, it forces those anchor regions to create a stretch of consecutive matches in the alignment resulting in a higher score for the correct alignment with a gap in the middle of the sequence. If the anchor sequence is not long enough, the score for the matching bases is not high enough, then the alignment will prefer a misalignment with the variant region aligning to the sequence between the variant and the end plus the attached anchor sequence.

Here we calculate the scores for the correct alignment as shown in scenario FIG. 1c. For a deletion of length v, having a distance to an end of the sequencing read d, and anchor length a, the alignment score can be calculated as the following.

$$\text{correct alignment score} = GO + GE \cdot v + m \cdot (a+d). \quad \text{(Equation 1)}$$

GO is the penalty for a gap opening, GE is the penalty for a gap extension, and m is the score for a match. The score for the misalignment is calculated as the following.

$$\text{misalignment score} = mm \cdot (a+d). \quad \text{(Equation 2)}$$

mm is the penalty for a mismatch.

In the second alignment using anchor sequences, the correct alignment score must be greater than the misalignment score. This can be written as Equation 3 below.

$$GO + GE \cdot v + m \cdot (a+d) > mm \cdot (d+a) \quad \text{(Equation 3)}$$

Rearranging Equation 3 results in Equation 4.

$$a > \frac{-GO - GE \cdot v}{m - mm} - d \quad \text{(Equation 4)}$$

The above scenario assumes that the region between the variant and the end of the sequencing read plus the anchor sequence result in mismatches with the region where the variant occurred. However, some nucleotides in this region may result in a match by chance. This depends on the sequence context in the variant, region from the variant to the end of the sequencing read, and the anchor sequence. Here we consider the scenario when there is a partial match in this sequence region. When the proportion of matching bases in the anchor sequence and the sequence between the variant and the end of the sequencing read is p, the misalignment score is the following.

$$\text{misalignment score} = (1-p) \cdot mm \cdot (a+d) + p \cdot m \cdot (d+a).\quad \text{(Equation 5)}$$

Again, the correct alignment score must be greater than the misalignment score, which can be written as Equation 6 below.

$$GO + GE \cdot v + m \cdot (a+ > (1-p) \cdot mm \cdot (a+d) + p \cdot m \cdot (d+a)\quad \text{(Equation 6)}$$

Rearranging Equation 6 results in Equation 7.

$$a > \frac{-GO - GE \cdot v}{(1-p) \cdot (\cdot m - mm)} - d \quad \text{(Equation 7)}$$

Plugging in real numbers to Equation 7, the anchor length for the example sequence shown in FIG. 1 can be determined as the following. With the following alignment parameters: gap opening penalty as −6, gap extension penalty as −1, match score as 1, mismatch penalty as −0.225, the anchor length should be at least 15 nucleotides.

This example provides a general guideline for how long an anchor sequence should be designed. Only the basic parameters for sequence alignment were taken into account in this example. However, when more sophisticated parameters are included, such as base quality score and position of each base within the sequence, the calculation changes. We note that the minimal length of an anchor sequence depends on the sequence context in the variant, anchor, and the sequence in between the two. We also note that p is a parameter that describes the sequence context near the variant. By selecting anchor sequences with low sequence identity to the target sequence, especially near the end of an amplicon, p can generally be controlled to be less than 0.5.

Example 3. Determination of the Minimal Length Required for Anchor Sequences

In this example, we aim to determine the minimal length required for the anchor sequences using several clinical relevant sequences. By using several clinical relevant sequences, we determine the minimal length of anchor sequence across different sequence context. Five sequences are shown and listed in Table 2. For each sequence listed, the sequence underlined were deleted resulting in a sequence variant. Sequencing reads from deep sequencing are simulated using CuReSim1.3 (http://www.pegase-biosciences.com/curesim-a-customized-read-simulator/) with the following parameters: m set as the length of the amplicon, sd set as 3 and parameters d, i and s are all set as 0 to simulate the sequencing process including sequencing error. To simulate the case with a total depth of 1000× and 20% variant allele frequency, the parameter n is set to 800 and 200 for wildtype and mutant alleles, respectively. The wildtype alleles and mutant alleles are combined to simulate the sequencing reads from an experiment.

Anchor alignment was performed following the steps below. The sequence "NNNNN" (IUPAC code) was attached to both ends of the sequencing reads and the target sequence, which is the same sequence as the wildtype allele. The anchor sequences listed in Table 3 were attached to the 5'-end of the sequencing reads, and the reverse complement of those anchor sequences were attached to the 3'-end of the sequencing reads resulting in extended sequencing reads. The same anchor sequences were attached to the target sequence resulting in an extended target sequence. Sequence alignment was performed using BWA aligner v0.7.10 using the following parameters: bwa mem -k17 -W40 -r10 -A2 -B5 -O2 -E1 -L0. Variant calling was performed using Samtools v1.3.1 with the following parameters: samtools mpileup -d 1000000 -Q 0 -B. Table 3 shows the variant length, distance between the variant to the end of the sequencing read, and anchor length for each sequence tested. For each sequence, several anchor sequences have been tested and the shortest one is listed in Table 3. In each of these cases, if one nucleotide is removed from the anchor sequence, the variant cannot be identified using the anchor alignment and variant calling method described above.

TABLE 2

Sequences tested. The variant sequence is underlined.

| Case No | Gene | Mutation Type | Allele Frequency | Amplicon Sequence |
|---|---|---|---|---|
| 1 | KMT2D | Deletion | 0.5818 | GTGGTGGGGAAGCAGGT GAGTCCTCAGGTGGTGG GGATGTGGGGGAGTCCT CAGGTGGTGGGGAGAGG CGTGAAGCCTCAGGTGG AGGGGACGTGGGAGACT CCTCAGGCGGTGGGGA (SEQ ID NO: 4) |
| 2 | EGFR | Deletion | 0.2 | TAGGGACTCTGGATCCC AGAAGGTGAGAAAGTTA AAATTCCCGTCGCTATC AAGGAATTAAGAGAAGC AACATCTCCGAAAGCCA ACAAGGAA (SEQ ID NO: 5) |
| 3 | EGFR | Deletion | 0.09 | TAGGGACTCTGGATCCC AGAAGGTGAGAAAGTTA AAATTCCCGTCGCTATC AAGGAATTAAGAGAAGC AACATCTCCGAAAGCCA ACAAGGAA (SEQ ID NO: 6) |
| 4 | MET | Deletion | 0.4549 | CAAGCTCTTTCTTTCTC TCTGTTTTAAGATCTGG GCAGTGAATTAGTTCGC TACGATGCAAGAGTACA CACTCCTCATTTGGATA GGCTTGTAAGTGCCCGA AGTGTAAGCCCAACTAC AGAA (SEQ ID NO: 7) |
| 5 | MET | Deletion | 0.2 | GGCACTGGGTCAAAGTC TCCTGGGGCCCATGATA GCCGTCTTTAACAAGCT CTTTCTTTCTCTCTGTT TTAAGATCTGGGCAGTG AATT (SEQ ID NO: 8) |

TABLE 3

Parameters used to determine the minimal length of anchor sequence.

| Case No | Variant Length (v) | Distance to End (d) | Anchor Sequence Length (a) | Anchor Sequence |
|---|---|---|---|---|
| 1 | 27 | 17 | 8 | ATAATCAG |
| 2 | 7 | 4 | 4 | TTCC |
| 3 | 15 | 14 | 4 | TTCC |
| 4 | 16 | 7 | 6 | ATAATC |
| 5 | 8 | 4 | 4 | TTCC |

The invention claimed is:

1. A method of identifying a variant from a clinical sample by aligning a next generation sequencing (NGS) read to a reference sequence implemented on a NGS computing platform, comprising:
   (a) collecting a clinical sample from a human subject;
   (b) extracting nucleic acids from the clinical sample;
   (c) amplifying the nucleic acids by multiplexed polymerase chain reaction (PCR);
   (d) generating a NGS read of a gene;
   (e) performing a first alignment of the NGS read to a reference sequence;
   (f) identifying a target sequence within the reference sequence whereto the NGS read maps;
   (g) generating a first and a second anchor sequence;
   (h) generating an extended NGS read by attaching the first anchor sequence to the upstream region and the second anchor sequence to the downstream region of the NGS read respectively;
   (i) generating an extended target sequence by attaching the first anchor sequence to the upstream region and the second anchor sequence to the downstream region of the target sequence respectively;
   (j) matching the first anchor sequence of the extended NGS read to the first anchor sequence of the extended target sequence and the second anchor sequence of the extended NGS read to the second anchor sequence of the extended target sequence respectively;

(k) performing a second alignment of the extended NGS read to the extended target sequence, wherein a misalignment rate of the second alignment is lower than a misalignment rate of the first alignment;

(l) identifying a position on the extended NGS read that does not align with the extended target sequence based on the second alignment, wherein the position includes or lacks at least one base; and (m) calling a variant based on the position, wherein at least the steps of (d) generating the NGS read, (e) performing the first alignment and (k) performing the second alignment are conducted via a NGS computing platform.

2. The method of claim 1, wherein the NGS read comes from the clinical sample originating from cell line, biopsy, primary tissue, frozen tissue, formalin-fixed paraffin-embedded (FFPE), liquid biopsy, blood, serum, plasma, buffy coat, body fluid, visceral fluid, ascites, paracentesis, cerebrospinal fluid, saliva, urine, tears, seminal fluid, vaginal fluid, aspirate, lavage, buccal swab, circulating tumor cell (CTC), cell-free DNA (cfDNA), circulating tumor DNA (ctDNA), DNA, RNA, nucleic acid, purified nucleic acid, purified DNA, or purified RNA.

3. The method of claim 2, wherein the clinical sample originates from a patient having cancer, solid tumor, hematologic malignancy, rare genetic disease, complex disease, diabetes, cardiovascular disease, liver disease, or neurological disease.

4. The method of claim 1, wherein the reference sequence is a region within the consensus sequence of human genome or a region within the genome sequence of an individual human subject.

5. The method of claim 1, wherein the reference sequence is a sequence from a sample different from the sample where the NGS read is generated.

6. The method of claim 1, wherein a distance between the variant and an end of the NGS read is ≤30 nucleotides.

7. The method of claim 1, wherein the variant comprises an insertion or a deletion.

8. The method of claim 1, wherein the length of the variant is at least 12 nucleotides.

9. The method of claim 1, wherein the variant occurs in a region that is soft-clipped or a consecutive stretch of mismatches in the first alignment in step (e).

10. The method of claim 1, wherein the allele frequency of the variant is greater than the error rate of the sequencing instrument used to generate the NGS reads.

11. The method of claim 1, wherein the first anchor sequence or the second anchor sequence do not match to any part of the target sequence.

12. The method of claim 1, wherein the length of the first or the second anchor sequence is at least 4 nucleotides.

13. The method of claim 3, wherein a length of the first or the second anchor sequence is greater than $(-GO-GE \cdot v)/(m-mm)-d$, where v is a length of the variant, d is a distance between the variant and an end of the NGS read, GO, GE, m, and mm are gap opening, gap extension match, and mismatch scoring parameters for sequence alignment.

14. The method of claim 1, wherein a last nucleotide in the first anchor sequence or a first nucleotide in the second anchor sequence is IUPAC code N.

15. A method of identifying a human subject having a variant by aligning a next generation sequencing (NGS) read to a reference sequence, implemented on a NGS computing platform, comprising:

(a) collecting a clinical sample from a human subject;

(b) extracting nucleic acids from the clinical sample;

(c) amplifying the nucleic acids by multiplexed polymerase chain reaction (PCR);

(d) generating a NGS read of a gene, wherein the NGS read is no more than 500 nucleotides;

(e) performing a first alignment of the NGS read to a reference sequence;

(f) identifying a target sequence within the reference sequence whereto the NGS read maps;

(g) generating a first, and a second anchor sequences, wherein the anchor sequences is at least 4 nucleotides;

(h) generating an extended NGS read by attaching the first anchor sequence to the upstream region and the second anchor sequence to the downstream region of the NGS read respectively;

(i) generating an extended target sequence by attaching the first anchor sequence to the upstream region and the second anchor sequence to the downstream region of the target sequence respectively;

(j) matching the first anchor sequence of the extended NGS read to the first anchor sequence of the extended target sequence and the second anchor sequence of the extended NGS read to the second anchor sequence the extended target sequence respectively;

(k) performing a second alignment of the extended NGS read to the extended target sequence, wherein a misalignment rate of the second alignment is lower than a misalignment rate of the first alignment;

(l) identifying a position on the extended NGS read that does not align with the extended target sequence based on the second alignment, wherein the position includes or lacks at least one base;

(m) calling a variant based on the position, and the variant is at least 2 nucleotides;

(n) identifying a disease selected from the group consisting of cancer, cardiovascular disease, metabolic syndrome, neurological disease and immune status, wherein at least the steps of (d) generating the NGS read, (e) performing the first alignment and (k) performing the second alignment are conducted via a NGS computing platform.

16. The method of claim 15, wherein the disease is solid tumor or hematologic malignancy.

17. A method of identifying a human subject having a variant by aligning a next generation sequencing (NGS) read to a reference sequence, implemented on a NGS computing platform, comprising:

(a) collecting a clinical sample from a human subject;

(b) extracting nucleic acids from the clinical sample;

(c) amplifying the nucleic acids by multiplexed polymerase chain reaction (PCR);

(d) generating a NGS read of a gene;

(e) performing a first alignment of the NGS read to a reference sequence;

(f) identifying a target sequence within the reference sequence whereto the NGS read maps;

(g) generating a first, and a second anchor sequences;

(h) generating an extended NGS read by attaching the first anchor sequence to the upstream region and the second anchor sequence to the downstream region of the NGS read respectively;

(i) generating an extended target sequence by attaching the first anchor sequence to the upstream region and the second anchor sequence to the downstream region of the target sequence respectively;
(j) matching the first anchor sequence of the extended NGS read to the first anchor sequence of the extended target sequence and the second anchor sequence of the extended NGS read to the second anchor sequence the extended target sequence respectively;
(k) performing a second alignment of the extended NGS read to the extended target sequence, wherein a misalignment rate of the second alignment is lower than a misalignment rate of the first alignment;
(l) identifying a position on the extended NGS read that does not align with the extended target sequence based on the second alignment, wherein the position includes or lacks at least one base;
(m) calling a variant based on the position; and
(n) identifying a disease selected from the group consisting of cancer, cardiovascular disease, metabolic syndrome, neurological disease and immune status, wherein at least the steps of (d) generating the NGS read, (e) performing the first alignment and (k) performing the second alignment are conducted via a NGS computing platform.

* * * * *